United States Patent
Planard-Luong et al.

(10) Patent No.: US 10,173,072 B2
(45) Date of Patent: Jan. 8, 2019

(54) DEVICE AND METHOD FOR COSMETIC TREATMENT BY LIGHT

(71) Applicant: L'OREAL, Paris (FR)

(72) Inventors: Thi Hong Lien Planard-Luong, Bures sur Yvette (FR); Andre Beaufils, Montrodat (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/437,610

(22) PCT Filed: Oct. 22, 2013

(86) PCT No.: PCT/EP2013/072023
§ 371 (c)(1),
(2) Date: Apr. 22, 2015

(87) PCT Pub. No.: WO2014/064074
PCT Pub. Date: May 1, 2014

(65) Prior Publication Data
US 2015/0297912 A1    Oct. 22, 2015

Related U.S. Application Data

(60) Provisional application No. 61/756,044, filed on Jan. 24, 2013.

(51) Int. Cl.
*A61N 5/06* (2006.01)
*A61B 90/00* (2016.01)

(52) U.S. Cl.
CPC ........... *A61N 5/0616* (2013.01); *A61N 5/062* (2013.01); *A61B 2090/061* (2016.02);
(Continued)

(58) Field of Classification Search
CPC .................. A61N 5/0616; A61N 5/062; A61N 2005/0626; A61N 2005/0644;
(Continued)

(56) References Cited

U.S. PATENT DOCUMENTS 6,015,404 A    1/2000 Altshuler et al.
7,887,533 B2   2/2011 Barolet et al.
(Continued)

FOREIGN PATENT DOCUMENTS

DE    19647676 A1    5/1998
FR     2917299 A1   12/2008
(Continued)

OTHER PUBLICATIONS

International Search Report for PCT/EP2013/072023 (WO 2014/064074 A1), dated Dec. 18, 2013.
(Continued)

*Primary Examiner* — David C Eastwood
*Assistant Examiner* — Zahed Kabir
(74) *Attorney, Agent, or Firm* — The Marbury Law Group, PLLC

(57) ABSTRACT

The invention relates to a device for cosmetic treatment by light comprising:
  at least one light emission source (10);
  a reference surface (5) fixed with respect to said light emission source,
  at least one distance sensor (20) for measuring a distance between the reference surface (5) and a cosmetic treatment area (30) of the skin,
  a microcontroller (3) suitable for controlling the emission power of each light source (10), in which the emission power of each light source is slaved to the distance measured by the sensor.

13 Claims, 3 Drawing Sheets

(52) U.S. Cl.
CPC ............... *A61N 2005/0626* (2013.01); *A61N 2005/0644* (2013.01); *A61N 2005/0652* (2013.01); *A61N 2005/0659* (2013.01); *A61N 2005/0663* (2013.01)

(58) Field of Classification Search
CPC .... A61N 2005/0652; A61N 2005/0659; A61N 2005/0663; A61B 2090/061
USPC .................................. 607/88, 100; 606/2, 9
See application file for complete search history.

(56) References Cited

U.S. PATENT DOCUMENTS

| | | | | |
|---|---|---|---|---|
| 7,938,643 | B2* | 5/2011 | Rueggeberg | G01J 3/0251 433/215 |
| 8,057,525 | B2 | 11/2011 | Suzuki | |
| 2001/0021812 | A1* | 9/2001 | Lundahl | A61N 5/062 600/476 |
| 2002/0188218 | A1* | 12/2002 | Lipman | A61B 5/4824 600/557 |
| 2002/0191396 | A1* | 12/2002 | Reiff | F21L 4/04 362/246 |
| 2004/0167501 | A1 | 8/2004 | Island et al. | |
| 2005/0049582 | A1 | 3/2005 | DeBenedictis et al. | |
| 2005/0083687 | A1 | 4/2005 | Brass et al. | |
| 2006/0071245 | A1 | 4/2006 | Zhang | |
| 2006/0200116 | A1 | 9/2006 | Ferren et al. | |
| 2006/0293727 | A1* | 12/2006 | Spooner | A61N 5/0616 607/88 |
| 2007/0016269 | A1 | 1/2007 | Suzuki et al. | |
| 2007/0027510 | A1* | 2/2007 | Rodrigues | A61N 5/0621 607/88 |
| 2007/0185553 | A1* | 8/2007 | Kennedy | A61N 5/0616 607/100 |
| 2007/0255359 | A1 | 11/2007 | Neev | |
| 2007/0276359 | A1* | 11/2007 | Segal | A61N 5/06 606/11 |
| 2008/0030990 | A1 | 2/2008 | Hanney | |
| 2008/0058783 | A1* | 3/2008 | Altshuler | A61B 18/203 606/9 |
| 2008/0140164 | A1* | 6/2008 | Oberreiter | A61N 5/0616 607/88 |
| 2008/0212319 | A1 | 9/2008 | Klipstein | |
| 2010/0027257 | A1 | 2/2010 | Boonekamp et al. | |
| 2010/0039812 | A1 | 2/2010 | Cheng et al. | |
| 2010/0207131 | A1 | 8/2010 | Chiang et al. | |
| 2010/0274329 | A1 | 10/2010 | Bradley et al. | |
| 2010/0331929 | A1 | 12/2010 | Burrows et al. | |
| 2012/0215210 | A1* | 8/2012 | Brown | A61B 18/203 606/9 |
| 2014/0237845 | A1 | 8/2014 | Llim | |
| 2015/0035449 | A1* | 2/2015 | Williams | H05B 33/0815 315/250 |

FOREIGN PATENT DOCUMENTS

| | | |
|---|---|---|
| GB | 2443318 A | 4/2008 |
| JP | H06-254170 A | 9/1994 |
| JP | 2006-506126 A | 2/2006 |
| JP | 2007-020593 A | 2/2007 |
| JP | 2009-525769 A | 7/2009 |
| JP | 2009-532079 A | 9/2009 |
| JP | 2009-542330 A | 12/2009 |
| JP | 2010-162157 A | 7/2010 |
| KR | 10-1085937 B1 | 11/2011 |
| KR | 10-1103327 B1 | 12/2011 |
| WO | 2004/043543 A1 | 5/2004 |
| WO | 20051011606 A2 | 2/2005 |
| WO | 2007/106339 A2 | 9/2007 |
| WO | 2008/002625 A2 | 1/2008 |
| WO | 20081057640 A2 | 5/2008 |
| WO | 2012/086991 A2 | 6/2012 |
| WO | 2014/064075 A1 | 5/2014 |

OTHER PUBLICATIONS

International Search Report for PCT/EP2013/072024 (WO 2014/064075 A1), dated Nov. 26, 2013.
English language abstract for DE 19647676 (May 20, 1998).
English language abstract for FR 2917299 (Dec. 19, 2008).
English language abstract for KR 10-1085937 (Nov. 22, 2011).
English language abstract for WO 2012/086991 (Jun. 28, 2012).
Non-Final Office Action for co-pending U.S. Appl. No. 14/437,598, dated Aug. 15, 2016.
Japanese Office Action for counterpart Application No. JP 2015-538403, dated Sep. 15, 2015.
Final Office Action for copending U.S. Appl. No. 14/437,598, dated Feb. 13, 2017.
Non-Final Office Action for copending U.S. Appl. No. 14/437,598, dated Oct. 4, 2017.

* cited by examiner

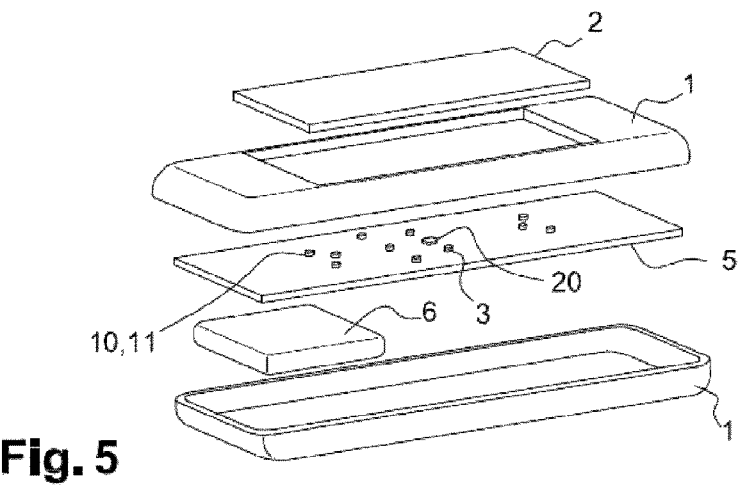
Fig. 5
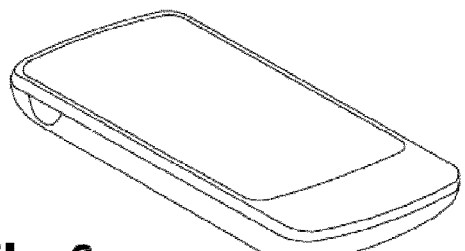
Fig. 6
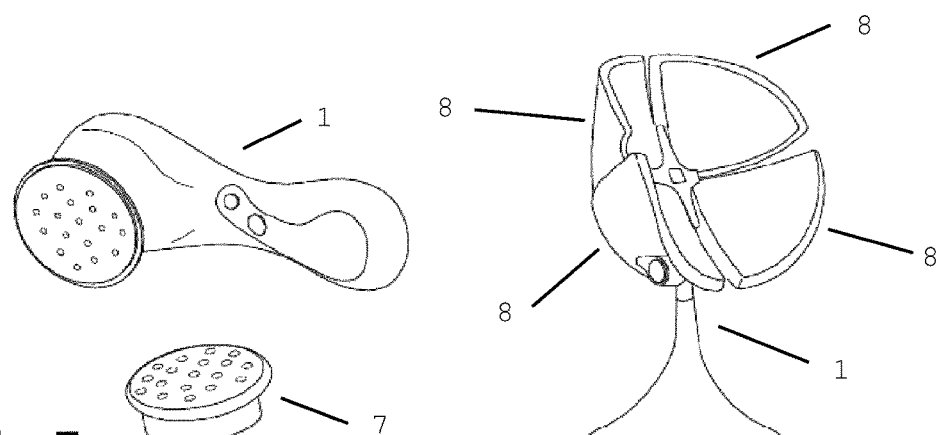
Fig. 7   Fig. 8

DEVICE AND METHOD FOR COSMETIC TREATMENT BY LIGHT

This is a national stage application of PCT/EP2013/072023, filed internationally on Oct. 22, 2013, which claims priority to U.S. Provisional Application No. 61/756,044, filed on Jan. 24, 2013, as well as French Application No. 1260060, filed on Oct. 23, 2012. The contents of the above-mentioned applications are expressly incorporated herein by reference in their entireties.

CONTEXT OF THE INVENTION

The present invention relates to a device for cosmetic treatment of the skin, i.e. non-therapeutic, especially by exposing an area of skin to light. The present invention also relates to an apparatus comprising such a device and a cosmetic method comprising the use of such an apparatus.

DISCUSSION OF THE PRIOR ART

There exist apparatuses for dermatological treatment of the skin by luminotherapy. For example, document U.S. Pat. No. 7,887,533 describes such an apparatus for professional use, by doctors especially. This apparatus comprises a system for assembling light-emitting diodes (LEDs) arranged in rows and coupled with cylindrical lenses. The lenses make it possible to tailor the angle of radiation of each light beam of the LEDs with greater or lesser flexibility. Document WO-A-2012/086991 describes an apparatus using several wavelengths concomitantly to treat various pathologies.

There also exist apparatuses for cosmetic treatment of the skin by exposure to light which are for private use. A user holds the apparatus in their hand and orients it so as to expose a given area of skin to a luminous radiation emitted by LEDs arranged in the apparatus. It is for example possible to cite the devices described in documents FR-A-2 917 299, US-A-2010/274329 or WO-A-2008/057640. The known apparatuses typically comprise one or more LEDs disposed in a casing. The number of LEDs is often significant so as to guarantee homogeneity of the treatment and the emission wavelength of the LEDs is chosen according to the applications envisaged. For example, document EP-A-1 648 385 proposes to use at least one first source emitting yellow light (with a dominant wavelength at about 590 nm) and at least one second source emitting infrared light (with a dominant wavelength at about 850 nm) with controlled powers for each source.

Devices for cosmetic treatment of the skin by light must envisage means for controlling the intensity of the radiation of the light on the surface to be treated (expressed in $mW/cm^2$). The intensity of the light must lie between a minimum value for efficacious treatment and a maximum value so as to avoid any damage caused by a too great exposure. This constraint is still stricter in apparatuses for private use (termed "Home devices"), for which the safety standards are higher.

In order to ensure optimal intensity of the light so as to, on the one hand, cause the desired effects on the skin, and on the other hand avoid any damage caused by a too great intensity, it is sought to control the distance between the luminous source and the treatment surface.

FIG. 1 schematically illustrates the radiation distributions obtained on an area of skin 30 exposed to light with various types of light-emitting diodes 15,16 emitting light beams 17,18 through a screen 2. For example, so-called "conventional" LEDs 15 emit a light beam 17 with a relatively small angular aperture, of the order of 15° to 20°. There must nonetheless be multiple such LEDs 15 in order to homogeneously cover the whole of an area 30 of skin to be treated. On the other hand, so-called "power" LEDs 16 (High-power LEDs or HPLEDs) emit a light beam 18 with a relatively large angular aperture, of the order of 120° to 140°—i.e. 60° to 70° in terms of angle of impact. By comparison with conventional LEDs, power LEDs are efficacious in terms of efficiency, lifetime and compactness.

FIG. 1 shows that the skin surface 30 exposed to light increases with the distance Δd between the device and the area to be treated, but the portion whose intensity (measured in $mW/cm^2$) is homogeneous is reduced. Indeed, the light beam 17, 18 emitted by an LED exhibits a pointlike radiation power over the whole of the illuminated area 30 that decreases in proportion to the illuminated surface. In the case of conventional LEDs, as the angle of impact is small, for the same variation of the distance the surface whose light intensity is homogeneous is reduced very little and its value is more stable; but in the case of HPLEDs, on account of their large angular aperture, the surface whose light intensity is homogeneous is greatly reduced and its value is smaller. This is why the treatment distance must be stricter for efficacious treatment.

Numerous commercial products provide means for avoiding too high an intensity but show little concern for the minimum threshold for efficacious treatment. In general, the usage instructions indicate that one should stand a certain distance away but there is not routinely any control procedure.

Certain commercial products provide for a mechanical abutment, such as LIPZOR™; or Luxe from BIOLUX™. This solution is simple to implement, but it compels contact of the abutment directly on the skin and therefore raises a hygiene problem. Moreover, if the device has to be moved over the surface to be treated, such usage is not practical on account of the friction on the skin.

The safety distance between the light source and the surface to be treated can be integrated into the device itself, thereby increasing the thickness of the device. For example, document KR-A-10-1103327 describes a compact device which unfurls at the moment of use so as to ensure a sufficient distance between the light source and the surface to be treated. Such a device is complex and expensive.

Document U.S. Pat. No. 7,887,533, mentioned above, comprises a distance sensor to allow adjustment before treatment. During treatment, the device must be stationary, otherwise the adjustment is lost. Such a solution, though it is suitable for an apparatus for professional medical use, is not suitable for private cosmetic use.

SUMMARY OF THE INVENTION

There therefore exists a need for a device for cosmetic treatment by light which makes it possible to ensure optimal intensity of the light on the area to be treated and which is compact and inexpensive.

For this purpose, the invention proposes to provide for a distance sensor in the device and to slave the emission power of each light source to the distance measured by the sensor. Slaving is intended to mean an increase or a decrease in the emission power of each light source as a function of the distance measured by the sensor. This continuous and real-time slaving of the power emitted by the light sources makes it possible to guarantee homogeneity of the luminous intensity on the area of skin to be treated throughout exposure. This gradual slaving of the intensity of the emitted power is complementary to the function of inhibiting and activating the power emitted by the light sources.

More specifically, the invention proposes a device for cosmetic treatment of the skin by light comprising:
- at least one light emission source;
- a reference surface fixed with respect to said light emission source,
- at least one distance sensor for measuring a distance between the reference surface and a cosmetic treatment area of the skin,
- a microcontroller suitable for controlling the emission power of each light source,
- in which the emission power of each light source is slaved to the distance (DIST) measured by the sensor.

More specifically, the microcontroller controls the emission power of each light source, by increasing or decreasing the latter, as a function of the distance (DIST) measured by the sensor.

According to one embodiment, the device according to the invention comprises a plurality of light emission sources, at least one first group of sources emitting a light at a first wavelength and at least one second group of sources emitting a light at a second wavelength.

According to one embodiment, the device according to the invention comprises a plurality of distance sensors distributed in the body of the device.

According to one embodiment, the electronic unit of the device is suitable for interrupting the emission of each light source when the distance measured by the sensor is less than a first threshold and/or greater than a second threshold; for example, a sensory information element can be activated when the emission of at least one light source is interrupted.

According to one embodiment, the distance sensor constitutes a tactile button for controlling a program for operating the device.

According to one embodiment, each light source of the device is surface-mounted on an electronic card.

The device according to the invention makes it possible to control the homogeneity of the luminous intensity applied to the treatment area in the span of about +/−10%.

The invention also relates to an apparatus for cosmetic treatment, comprising a body and a device for cosmetic treatment by light according to the invention. Such an apparatus can exhibit various forms with a view to various applications. For example, the device for cosmetic treatment by light can be a nozzle suitable for being mounted in a reversible manner on the body of the apparatus; or the device can constitute an insert arranged on the body of the apparatus; or else the device can be housed in the body of the apparatus.

The subject of the invention is also an assembly—or kit—comprising a receptacle—pot, bottle, tube or other—of a cosmetic composition and an apparatus for cosmetic treatment by light according to the invention. The cosmetic composition of such a kit can be chosen from among a care product for oily skin and/or an anti-aging care product.

The subject of the invention is furthermore a cosmetic method comprising the implementation of the device for cosmetic treatment by light according to the invention. Advantageously, the cosmetic method comprises a step of applying a cosmetic composition, at least on an area of skin exposed to the luminous radiation of the device according to the invention.

BRIEF DESCRIPTION OF THE DRAWINGS

Other characteristics and advantages of the present invention will emerge on reading the detailed description which follows, given with reference to nonlimiting embodiments and illustrated by the appended drawings in which:

FIG. 5 shows an exploded view of a first exemplary apparatus for cosmetic treatment according to the invention, FIG. 6 shows the apparatus of FIG. 5;

FIG. 7 shows a second exemplary apparatus for cosmetic treatment according to the invention, and FIG. 8 shows a third exemplary apparatus for cosmetic treatment according to the invention.

The appended figures are provided solely by way of illustration and to facilitate the understanding of the invention. Not all the figures are represented to scale and certain elements of the devices and apparatuses described may not be represented in the figures.

DETAILED DESCRIPTION OF THE INVENTION

The invention relates to a device for cosmetic treatment by light. The device of the invention comprises at least one light emission source (designated LED subsequently) and a reference surface fixed with respect to said LED; for example the reference surface can be a screen of the device or an electronic card on which said LED is placed. Each LED emits a light beam with a given power and a given angular aperture and this beam is transmitted toward an area of skin to be treated. The question of the effectiveness of the treatment and of the homogeneity of the radiation over the area of skin to be treated arises, especially at the periphery of the area. For this purpose, the device according to the invention furthermore comprises a distance sensor for measuring a distance between the reference surface and the area of skin to be treated so as to allow a slaving of the emission power of the LED to the measured distance.

Figures 1A, 1B:
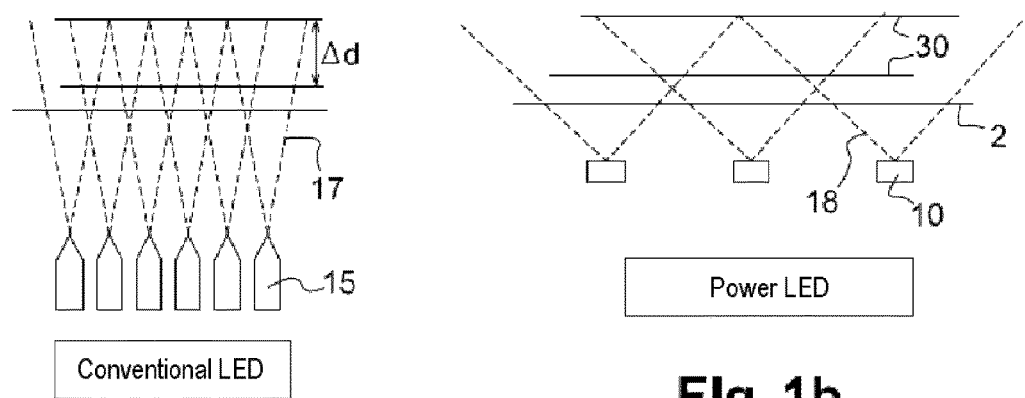
FIG. 1, already described, schematically illustrates the radiation distributions obtained with various types of light-emitting diodes.
Figure 2:
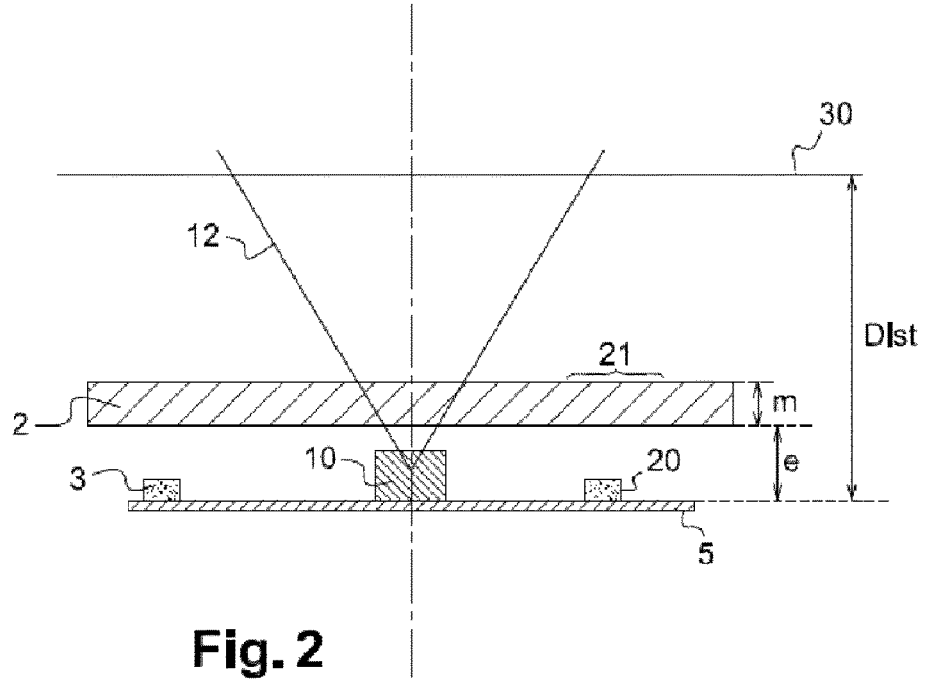
FIG. 2 shows a detail of a device according to one embodiment of the invention.

FIG. 2 shows a detail of a device according to one embodiment of the invention. FIG. 2 depicts an LED 10 emitting a light beam 12 through a screen 2 toward an area of skin 30 to be treated. FIG. 2 also shows an electronic card 5 on which is positioned the LED and a distance sensor 20 arranged on the electronic card 5. The electronic card 5 also comprises a microcontroller 3 which receives the data measured by the sensor 20 and which controls the operation of the LED 10. In particular, the microcontroller controls the turning on and the turning off of the LED 10, as well as its mode of emission (pulsed or continuous light) according to programs which can be predefined or programmed by the user. The microcontroller 3 also controls the emission power of the LED. In particular, according to the invention, the microcontroller controls the emission power of the LED as a function of the measurements provided by the distance sensor 20.

It is understood that the expression "microcontroller" is intended to mean a single electronic device, such as for example a microprocessor chip, or to mean an assembly of programmable electronic elements, such as for example communication gateways allowing management by a third party item of equipment (such as PC, PDA, etc.).

The LED 10 can be an HPLED or a so-called conventional LED; the LED can be monochromatic (i.e. its emission spectrum comprises a unique dominant wavelength peak), or multi-chromatic (i.e. its emission spectrum comprises several quasi-monochromatic lights, for example two). The LED 10 and/or the sensor 20 can be of "surface-mounted components" (SMC) type for better integration with the electronic card 5.

The LED is designed to emit a light beam 12 with a given spectrum of wavelengths and a given angular aperture. The LED can be designed to emit light in a continuous and/or pulsed manner in a given power range. The mode of emission and the emission power of the LED are controlled by the microcontroller which pilots the operation of the LED.

The LED 10 is fixed with respect to the electronic card 5 on which it is arranged; the LED 10 is also fixed with respect to the screen 2 of the device. The distance e between the electronic card 5 and the internal surface of the screen 2 is known and controlled while assembling the device and the thickness m of the screen 2, as well as its refractive index, are known. The surface covered by the light beam 12 of the diode on the area of skin to be treated 30 therefore depends solely on the distance DIST between a reference surface of the device and the treatment area 30; such a reference surface is represented by the electronic card 5 in FIG. 2 but could also be the internal or external surface of the screen 2 or any other surface fixed with respect to the LED. The sensor 20 therefore measures directly or in a derived manner the distance DIST between the reference surface 5 and the area of skin to be treated 30 and transmits its measurement DIST to the microcontroller 3 which adapts the control of emission power of the LED 10 as a function of this distance DIST.

Figure 3:
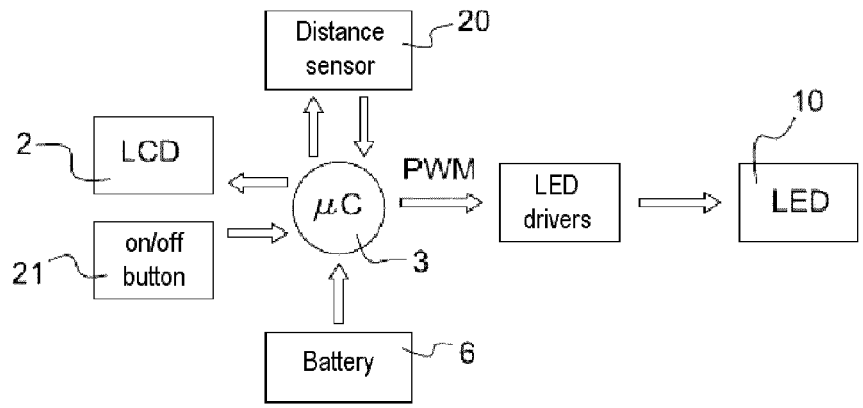
FIG. 3 represents a schematic diagram of an electronic card used in a device according to the invention.

FIG. 3 is a schematic diagram of an electronic card 5 used in the device according to the invention. The microcontroller 3 is supplied by a battery 6 and receives the data measured by the distance sensor 20. The microcontroller 3 also receives on/off commands and programming commands on the basis of a button 21 actuated by the user. Such a button 21 can be mechanical or tactile. The microcontroller 3 can also control the display of information on a screen 2, so as to allow the user to view the mode of operation of the device. It is also seen in FIG. 3 that the LEDs 10 are controlled by the microcontroller 3, for example by means of pulse with modulated (PWM) signals. The command dispatched from the microcontroller 3 to each LED 10 comprises at least one value of emission power.

Figure 4:
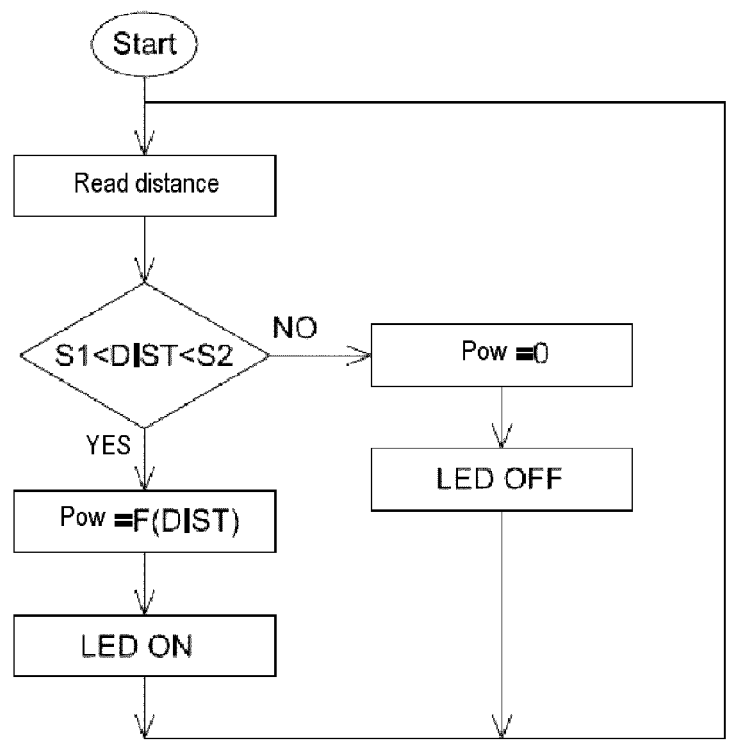
FIG. 4 represents a flowchart of a program implemented by the microcontroller of the device according to the invention.

FIG. 4 represents a flowchart of a program implemented by the microcontroller of the device according to the invention. When the device is activated (START) and a program chosen by the user, the microcontroller recovers a distance reading datum via the distance sensor. If the distance DIST lies between two threshold values S1 and S2; the microcontroller commands the emission of light by the LEDs (LED ON) with a given power dependent on the measured distance.

If the distance DIST is less than a first threshold S1 or greater than a second threshold S2, the microcontroller turns off the emission of light by the LEDs (LED OFF). For example, the first threshold S1 can be fixed at 15 mm and the second threshold S2 can be fixed at 45 mm; the treatment being considered to be ineffective beyond 35 mm and the exposure being considered to be potentially harmful short of 15 mm. The device can include a vibrator and/or a telltale light and/or a loudspeaker can inform the user in a sensory manner that the luminous emission of at least one source has been interrupted because the device is held too close or too far from the treatment area.

On the other hand, if the distance DIST does indeed lie between the two threshold values S1 and S2; the microcontroller controls the power of each LED as a function of the measured distance: Pow=F(DIST). More specifically, the emission power of each LED can obey a specific slaving law dependent on the location of the LED in the device (central or peripheral position) and/or dependent on the type of LED (conventional or power LED) and/or dependent on its dominant emission wavelength. The power of each LED will thus be increased or decreased as a function of the distance measured by the distance sensor.

In one embodiment (illustrated in FIG. 2), the distance sensor 20 can constitute a tactile button for controlling the operation of the device. The distance sensor 20 is situated at a distance e from the screen which is markedly less than the minimum threshold value S1. The screen 2 area situated just above the sensor 20 can be delineated on the screen so as to guide the user toward the tactile button 21. Thus, if a user contacts the tactile button area 21 with their finger, the sensor 20 detects a distance DIST less than the first threshold S1 and interrupts the emission of the LEDs if appropriate. Nonetheless, the distance DIST measured by the sensor 20 during a contact with the tactile button 21 is substantially equal to a known and fixed distance (e+m) which is then interpreted by the microcontroller 3 as a press on the button 21. Such a press, or a series of presses, can be interpreted by the microcontroller 3 so as to control a program for operating the device.

According to one embodiment, provision may be made for a plurality of distance sensors arranged in the device, distributed between the various LEDs so as to provide the microcontroller with the precise distance measurements for each LED; especially in the case of a non-plane area of skin to be treated and/or of a user who held the device in their hand with a poorly adopted orientation. Each distance sensor would thus provide a measurement which would be used by the microcontroller to precisely control the emission power of a given group of LEDs.

In one embodiment, the device for cosmetic treatment by light according to the invention can comprise at least two groups of LEDs emitting respectively at two different wavelengths. When two types of LED emitting at two different wavelengths are used in a concomitant manner, it is necessary to guarantee a precise power of luminous radiation per unit of exposed skin for each type of wavelength. The device according to the invention makes it possible to precisely tailor the emission power of each LED so as to ensure a controlled luminous intensity on the area of skin to be treated. It then becomes possible to ensure the homogeneity of the radiations of the two types of LED over the area to be treated without necessarily using the same number of LEDs of each type.

FIGS. 5 and 6 illustrate an exemplary application in which the device for cosmetic treatment by light is integrated into an apparatus; FIG. 5 is an exploded view and FIG. 6 is a view of the apparatus assembled.

FIG. 5 shows that the LEDs 10 can be arranged on an electronic card 5, for example by using LEDs of "surface-mounted components" (SMC) type. The apparatus exhibits a body 1 consisting of a shell exhibiting a front face furnished with the screen 2 and a rear face. The shell of the body 1 makes it possible to house the card 5 carrying the LEDs 10 as well as other electronic components and a battery 6. The electronic card 5 also carries the distance sensor 20 suitable for measuring the distance DIST mentioned with reference to FIG. 2 as well as the microcontroller 3 which controls the modes of operation of the apparatus according to programs activated by the user by means of an interface provided on the body 1. Any type of program can be envisaged within the framework of this invention to control pulsed and/or continuous and/or alternated emissions of light. In particular, the microcontroller controls the emission power of each LED 10 as a function of the data received from the distance sensor(s) 20 and according to the specifics of each LED.

In the example of FIGS. 5 and 6, the LEDs of a first type are more than doubled with respect to the LEDs of a second type even though the area to be treated remains substantially covered in the same manner by the radiations of the two types of LED. It is thus possible to optimize the costs while not using the same number of LEDs of each type. For example, it is possible to envisage exposing an area of skin to a first luminous radiation by means of ten LEDs emitting light beams at the wavelength of 590 nm with an intensity of 2.1 mW/cm$^2$ of exposed skin, and simultaneously, exposing the area of skin to a second luminous radiation by means of four LEDs emitting light beams at the wavelength of 870 nm with an intensity of 0.5 mW/cm$^2$ of exposed skin. The specific control of the power of each LED as a function of the distance from the treatment area makes it possible to ensure good homogeneity of all of the radiations with a controlled intensity for each radiation.

FIG. 7 illustrates another exemplary application in which the device for cosmetic treatment by light constitutes a nozzle 7 that can be fitted and removed. The apparatus comprises a body 1 which can exhibit the form of a handle and which can house a battery. The microcontroller for controlling the operation of the LEDs can be housed in the body 1 or in the nozzle 7.

FIG. 8 illustrates yet another exemplary application in which the device for cosmetic treatment by light constitutes an insert 8 arranged on the apparatus. The apparatus comprises a body 1 which can exhibit the form of a support and which can house a battery. The microcontroller for controlling the operation of the LEDs can be housed in the body 1 or in each insert 8. In FIG. 8, it is seen that a plurality of inserts 8 is inserted on the support 1.

The invention also pertains to an assembly comprising a receptacle (pot, tube or other) of a cosmetic composition and a cosmetic treatment apparatus such as described above. The cosmetic composition can be chosen from among a care product for oily skin and/or an anti-aging care product, for example a composition containing hydrophobic silica aerogel particles.

EXAMPLE

According to a first exemplary implementation, a device comprising ten LEDs at 590 nm and four LEDs at 870 nm is used. The LEDs at 590 nm exhibit an angular aperture of 120° and the LEDs at 870 nm exhibit an angular aperture of 140°. The distance (designated e in FIG. 2) between the screen and the LEDs is 0.5 mm and the distance (designated DIST in FIG. 2) between the LEDs and the area of skin to be treated 30 is measured continuously by a sensor 20 situated substantially at the center of the device. The screen exhibits a refractive index of 1.586 and the thickness (designated m in FIG. 2) of the screen is 1.5 mm. The power of each LED is slaved continuously to the distance DIST measured by the sensor. By virtue of prior optical studies on the system, it is possible to deduce a function for slaving the power of each LED in relation to the measured distance DIST so as to obtain a stable and homogeneous global power over the surface to be treated.

Such an arrangement of the device according to the invention makes it possible to treat in a homogeneous manner with two different types of radiation an area of skin of about 42 cm$^2$ a distance of 40 mm away and of about 32 cm$^2$ a distance of 20 mm away.

The present invention has been described with reference to particular embodiments, illustrated in FIGS. 1 to 8, and with reference to particular examples, but it is understood that other variants can be envisaged by the person skilled in the art, especially the number and the types of LED can vary and arrangements and dimensions other than those described in FIGS. 5 to 8 can be envisaged to constitute apparatuses according to the invention.

The invention claimed is:

1. A device for cosmetic treatment by light comprising:
   light emission sources comprising:
      first light emission sources that emit a first dominant wavelength of light; and
      second light emission sources that emit a second dominant wavelength of light different from the first dominant wavelength;
   a reference surface fixed with respect to the light emission sources;
   distance sensors disposed adjacent to the light emission sources for measuring a distance between each light emission source and a cosmetic treatment area; and
   a microcontroller configured to increase or decrease the emission power of each light emission source as a function of the distances measured by the distance sensors, the dominant wavelength of each light emission source, and a location of each light emission source in the device, such that a luminous intensity of light emitted from the device is substantially homogeneous over the cosmetic treatment area.

2. The device of claim 1, wherein the microcontroller is configured to interrupt the emission of each light source when the distance measured by the sensor is less than a first threshold and/or greater than a second threshold.

3. The device of claim 2, further comprising a sensory information element activated when the emission of at least one light source is interrupted.

4. The device of claim 1, wherein the distance sensor comprises a tactile button for controlling a program for operating the device.

5. The device of claim 1, wherein the reference surface comprises an electric card upon which the light emission sources are surface-mounted.

6. An apparatus for cosmetic treatment by light, comprising:
   a body; and
   a cosmetic treatment device comprising:
      light emission sources comprising:
         first light emission sources that emit a first dominant wavelength of light; and
         second light emission sources that emit a second dominant wavelength of light different from the first dominant wavelength;
      a reference surface fixed with respect to the light emission sources;
      distance sensors disposed adjacent to the light emission sources for measuring a distance between each light emission source and a cosmetic treatment area; and
      a microcontroller configured to increase or decrease the emission power of each light emission source as a function of the distances measured by the distance sensors, the dominant wavelength of each light emission source, and a location of each light emission source in the device, such that a luminous intensity of light emitted from the device is substantially homogeneous over the cosmetic treatment area.

7. The apparatus of claim 6, wherein the device is housed in the body of the apparatus.

8. The apparatus of claim 6, wherein the device comprises a nozzle suitable for being mounted in a reversible manner on the body.

9. The apparatus of claim 6, wherein the device comprises an insert arranged in a support of the body.

10. The apparatus of claim 6, further comprising a receptacle for a cosmetic composition.

11. The apparatus of claim 10, wherein the cosmetic composition is chosen from a care product for oily skin and/or an anti-aging care product.

12. A method of cosmetic treatment, the method comprising:
    exposing light to an area to be treated by implementing a device comprising:
       light emission sources comprising:
          first light emission sources that emit a first dominant wavelength of light; and
          second light emission sources that emit a second dominant wavelength of light different from the first dominant wavelength;
       a reference surface fixed with respect to the light emission sources;
       distance sensors disposed adjacent to the light emission sources for measuring a distance between each light emission source and a cosmetic treatment area; and
       a microcontroller configured to increase or decrease the emission power of each light emission source as a function of the distances measured by the distance sensors, the dominant wavelength of each light emission source, and a location of each light emission source in the device, such that a luminous intensity of light emitted from the device is substantially homogeneous over the cosmetic treatment area.

13. The method of cosmetic treatment of claim 12, further comprising applying a cosmetic composition to the area to be treated.

* * * * *